(12) United States Patent
Aramant et al.

(10) Patent No.: US 8,057,483 B2
(45) Date of Patent: Nov. 15, 2011

(54) SUBRETINAL IMPLANTATION INSTRUMENT

(75) Inventors: Robert B. Aramant, Crestwood, KY (US); Magdalene J. Seiler, Orange, CA (US)

(73) Assignee: Ocular Transplantation LLC, Crestwood, KY (US)

( * ) Notice: Subject to any disclaimer, the term of this patent is extended or adjusted under 35 U.S.C. 154(b) by 274 days.

(21) Appl. No.: 12/378,326

(22) Filed: Feb. 14, 2009

(65) Prior Publication Data
US 2010/0211079 A1 Aug. 19, 2010

(51) Int. Cl.
*A61F 9/00* (2006.01)

(52) U.S. Cl. ...................................... 606/107

(58) Field of Classification Search .............. 604/27, 604/35, 36, 38, 20, 28, 48, 60, 294, 239, 604/506, 164.01, 57–59; 606/4, 5, 6, 107, 606/161, 232, 108, 139, 144–148, 151–158, 606/186; 623/6.12, 4.1, 6.63; 81/9.22
See application file for complete search history.

(56) References Cited

U.S. PATENT DOCUMENTS

| | | | | |
|---|---|---|---|---|
| 3,016,895 A * | 1/1962 | Sein | ................ | 604/60 |
| 5,180,362 A * | 1/1993 | Worst | ................ | 604/8 |
| 5,217,465 A * | 6/1993 | Steppe | ................ | 606/107 |
| 5,817,075 A | 10/1998 | Giungo | | |
| 5,868,728 A | 2/1999 | Giungo et al. | | |
| 5,941,250 A | 8/1999 | Aramant | | |
| 5,962,027 A | 10/1999 | Hughes | | |
| 6,036,678 A | 3/2000 | Giungo | | |
| 6,045,791 A | 4/2000 | Liu | | |
| 6,053,899 A * | 4/2000 | Slanda et al. | ................ | 604/500 |
| 6,156,042 A | 12/2000 | Aramant | | |
| 6,159,218 A * | 12/2000 | Aramant et al. | ................ | 606/107 |
| 6,579,256 B2 | 6/2003 | Hughes | | |
| 2002/0016602 A1 * | 2/2002 | Li et al. | ................ | 606/139 |
| 2002/0156500 A1 * | 10/2002 | Storz-Irion et al. | ................ | 606/232 |
| 2003/0004491 A1 * | 1/2003 | Tenhuisen et al. | ................ | 604/502 |
| 2003/0054023 A1 * | 3/2003 | Hughes | ................ | 424/428 |
| 2004/0199140 A1 * | 10/2004 | Rue et al. | ................ | 604/506 |
| 2007/0027452 A1 * | 2/2007 | Varner et al. | ................ | 606/107 |

* cited by examiner

*Primary Examiner* — S. Thomas Hughes
*Assistant Examiner* — David Eastwood
(74) *Attorney, Agent, or Firm* — Raggio & Dinnin, P.C.

(57) ABSTRACT

An instrument for implanting tissue in an eye or other body member is disclosed. The instrument includes an elongated mandrel and a tubular nozzle arranged over the mandrel. The instrument also includes a piston engaging an end of the nozzle and a vacuum passage arranged in the piston. The instrument also includes a body having a portion of the piston arranged therein with one end of the mandrel being secured to the body. The instrument also includes an actuator integrated with the body wherein the actuator interacts with the piston to control movement of the nozzle relative to the mandrel.

12 Claims, 5 Drawing Sheets

SUBRETINAL IMPLANTATION INSTRUMENT

FEDERAL RESEARCH STATEMENT

The U.S. Government has a paid up license in this invention and the right in limited circumstances to require the patent owner to license others on reasonable terms as provided for by the terms of Contact No. 5R44EY015584 awarded by the National Institute of Health, National Eye Institute.

BACKGROUND OF THE INVENTION

The present invention relates to an instrument for implanting delicate tissue and/or materials in the human body, and more particularly to an instrument for surgically restoring eye sight by implanting fetal or other types of retinal tissue into the subretinal space in the back of the eye.

Most common eye problems, for example, myopia (nearsightedness), hyperopia (farsightedness), astigmatism (asymmetrical cornea) and presbyopia (the inability to focus on an object at close range) are due to errors in the refraction of light by the lens and cornea in the anterior part of the eye. Generally, these problems can be corrected by glasses, contact lenses, or corrective surgery.

However, blindness is most commonly due to damage of the retina in the back of the eye and, more specifically, is caused by abnormal function of cells bordering the subretinal space under the retina.

The transparent, layered retina processes light images projected by the cornea and lens. The photoreceptor layer in the back of the retina transforms the light into electrical impulses. Other retinal layers transfer these impulses through the optic nerve to the brain which interprets the impulses into what we perceive as sight.

The subretinal space is the area between the retinal pigment epithelium (RPE) and the photoreceptors of the retina. Normally, the photoreceptors are in close contact with the RPE. The RPE has many functions. It provides nutrition for the photoreceptors, and also removes waste products from the photoreceptors. In a normal eye, there are no blood vessels in the subretinal space. However, in some retinal diseases, blood vessels and connective tissue can grow in the space and cause blindness. The waste products from the photoreceptors accumulate and create a barrier for the nourishment from the RPE. The photoreceptors will then degenerate, resulting in vision loss or blindness, while the other layers of the retina can remain functional. By replacing the diseased RPE and/or photoreceptors that can hook up to the functional part of the retina, vision may be restored.

The most frequent cause of legal blindness is macular degeneration and retinitis pigmentosa. The macula is located in the back of the eye in the central portion of the retina and is responsible for central vision. In patients with macular degeneration, there is initially a dysfunction of the RPE in the macular region, which later leads to ingrowth of blood vessels and destruction of the light sensitive photoreceptors in the overlying retina. This results in impairment of central vision. Age related macular degeneration is an example of an eye disease that can be helped by using the herein disclosed method and instrument. The vision loss can be delayed and vision can be restored to a degree we now do not know the extent of.

Retinitis pigmentosa is a term for genetically caused photoreceptor degeneration. In these patients, the RPE and the photoreceptors must be replaced. Again, the method and instrument of the present invention can be utilized for such procedures.

It is to be noted that the surgical correction of diseases in the subretinal space between the retina and the RPE is rendered extremely difficult by the environment in which the surgery must take place. Moreover, the surgical procedure disclosed herein to implant fetal retinal tissue into the subretinal space of the eye is complicated by the fact that the fetal retinal tissue is in the nature of a transparent mass and extremely fragile.

Therefore, there is a need in the art for an improved subretinal implantation instrument and methodology for implanting such tissue inside the subretinal space.

SUMMARY OF THE INVENTION

According to the present invention, the foregoing and other objects and advantages are obtained by a novel design for an improved implantation instrument capable of handling fetal retinal tissue or other types of tissue and implants and placing this into the subretinal space between the retinal pigment epithelium and the retina of the eye.

In one type of implantation that occurs according to the present invention intact sheets of fetal retinal tissue which can be transplanted into the subretinal space and if necessary by flattening and protecting it by a gel that disintegrates and is subsequently absorbed by the recipient eye so as to leave the transplant free. The sheet transplant develops organized parallel layers resembling normal retina, with fully developed photoreceptors. The transplant can replace diseased photoreceptors and/or RPE. Moreover, the fetal retinal tissue is immunologically tolerated in the subretinal space and is not subject to rejection provided there is little surgical trauma. Other types of transplant tissue or implants may also be used and not just for the eye but in other portions of the body.

The instrument of the present invention comprises an elongated mandrel and a tubular nozzle arranged over the mandrel. It also comprises a piston engaging an end of the nozzle and a vacuum passage arranged in the piston to load the implant into the tip of the nozzle. The instrument also includes a body having a portion of the piston arranged therein, whereby one end of the mandrel is secured to the body. The instrument also comprises an actuator integrated with the body wherein the actuator interacts with the piston to control movement of the nozzle relative to the mandrel.

The advancement and retraction of the sleeve/nozzle, relative to the body or hand piece and mandrel, is controlled by the actuator mechanism on the hand piece, one element of which is a spring and another which is a button on one side of a peg. A coil spring is arranged around a portion of the piston and urges the piston in a rearward direction with relation to the body of the instrument. The actuator mechanism has an angled surface on a bottom surface of the button-peg that interacts with an angled surface on one end of the piston. This allows the surgeon/doctor who is using the instrument to keep their hands steady and use one hand to place the tissue in the predetermined position in the subretinal space. The releasing of the button by the finger tip of the surgeon allows the piston to be pushed back by the coil spring at a predetermined pace and in a smooth and controlled manner thus allowing the piston, which has the nozzle sleeve attached thereto, to be retracted and the tissue inside the tip of the nozzle to be placed into the target area during surgery. The unlocking of the nozzle with respect to the mandrel occurs by the surgeon fully pressing down the actuator button peg into the actuator spring to release the piston to allow for movement of the nozzle with respect to the mandrel. Thus the surgeon holds their hand completely still while the fingertip is in complete control of the delivery and the instrument, not pushing or injecting but placing the implant in the target area.

Mandrels and nozzles can be customized in different sizes and shapes for gentle implantation of different kinds of fragile tissue to the subretinal space in humans and as well as in different sizes of experimental animals. Examples of what can be implanted into the subretinal space of an eye are sheets of human retina, absorbent gels or microbeads containing different slowly releasing trophic factors or drugs, or electronic microchips. The whole instrument can be made in a disposable version. Alternatively, the hand piece can be made in an autocalveable reusable version, and mandrels and nozzles can be produced in sterile packages for one time use. Mandrels and nozzles can be designed in any known shape for implantation of any known tissue or implant in any known body part.

The details of the instrument and the methodology of using the instrument for the invention are more fully described in the following specification and drawings.

Other objects, features, and advantages of the present invention will become apparent from the subsequent description and appended claims, taken in conjunction with the accompanying drawings.

BRIEF DESCRIPTION OF THE PREFERRED EMBODIMENT(S)

Figure 1:
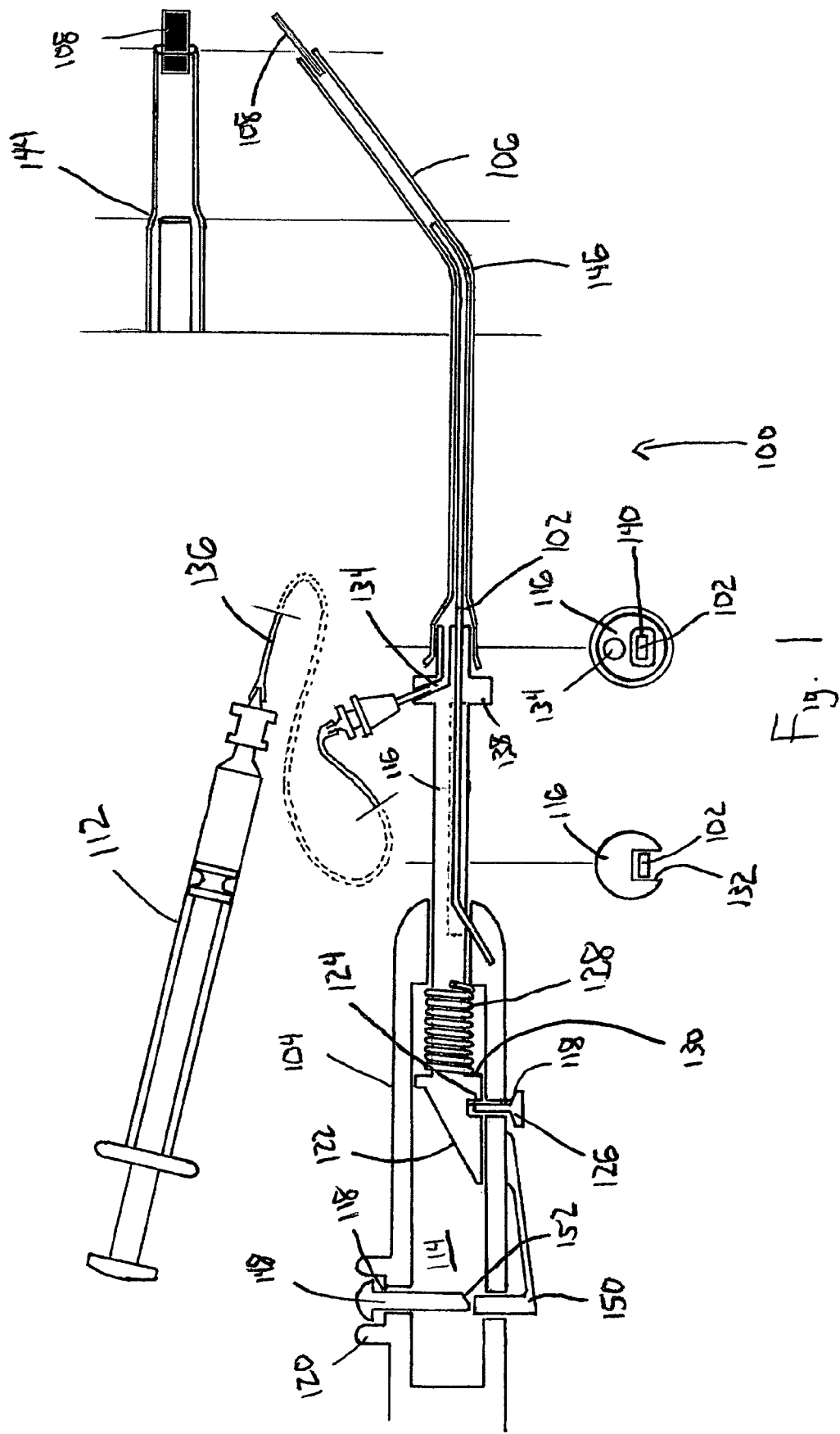
FIG. 1 shows a cross sectional front view of the subretinal implantation instrument in the loading position according to the present invention.

Referring to the drawings, it is shown the front of a subretinal implantation instrument 100 and methodology for the same according to the present invention.

The front of the eye 50 is covered by a transparent tissue, the cornea 52, surrounded by white conjunctiva tissue 54. The sclera 56 is a hard fibrous tissue that covers the exterior of the eyeball. The pupil 58 is the opening through which light passes to the back of the eye. The iris 60 changes the size of the pupil 58 to adjust to the amount of light. The transparent lens 62 is located behind the iris 60 and is suspended by a net of fibers 64. The fibers 64 are attached to the ciliary body 66. The part between the ciliary body 66 and where the retina 68 begins is called pars plana 70. The lens 62 focuses light rays onto the retina 68. The bulk of the eyeball 50 behind the lens 62 is formed by the vitreous chamber 72, which is filled with a colorless, gelatin like substance.

The retina 68 covers most of the walls of the vitreous chamber 72 and comprises transparent layers that extend forwardly to the pars plana 70 and which processes light images projected from the cornea 52 and the lens 62.

The rear of the retina 68 contains photoreceptors 74, which transform light into electrical impulses. The electrical impulses are carried by nerves in the retina 68 to the optic nerve 76, which, in turn leads to the brain. A monolayer of cells termed the retinal pigment epithelium (RPE) 77 resides behind the retina 68. The choroid 78 is a layer of blood vessels between the RPE 77 and sclera 56 that supplies oxygen and nutrients essential to the function of the retina 68. The RPE 77 transports these nutrients to the retina 68 and maintains a barrier between the choroid 78 and retina 68.

The region between the retina 68 and the RPE 77 is called the subretinal space 80. Normally, there is no "space". However, the retina 68 detaches very easily from the RPE 77 and it is in this "space" that the surgeon transplants a new piece of retinal tissue to replace damaged retina including photoreceptors 74 and/or RPE 77.

The fovea 82 is a small depression in the center of the retina 68 that is essential for sharp (focused) vision as well as color vision. The small area surrounding the fovea 82 is known as the macula 84 and is responsible for central vision. The point at which the object nerve 76 leaves the retina 68 on its way to the brain is called the optic disc 86.

In accordance with the present invention, surgical correction of retinal diseases in the subretinal "space" between the retina 68 and the RPE 77 is facilitated by a novel implantation subretinal instrument 100. The instrument 100 according to the present invention will deliver the tissue and without any movement of the surgeon. The surgeon will hold his or her hand completely still. The instrument has a mandrel 102 that is fixed to the hand piece or body 104 and a moveable sleeve 106 that contains the tissue 108 therein. When the sleeve 106 with the tissue 108 inside the tip is retracted, the tissue 108 is placed, not pushed or injected, into the target area, which is generally the subretinal space of the eye 50. This improved subretinal implantation instrument 100 has an actuator 110 that is integrated into the hand piece 104 and is not generally located on the outer surface such as those with a big spring outside of the hand piece as found in prior art implantation instruments. Furthermore, the subretinal implantation instrument 100 has a suction mechanism wherein the tissue 108 is picked up inside the nozzle sleeve 106 by controlled suction from an attached syringe 112. Once the tissue 108 is inside the nozzle 106 and secured therein, the syringe 112 can be detached by the surgeon during further surgical procedures with the subretinal implantation instrument 100.

The instrument 100 generally comprises a body or hand piece 104, wherein the body or hand piece 104 generally has a cylindrical shape. The body or hand piece 104 may have an inner bore or interior chamber 114 therein. The inner bore 114 may have a reduced diameter portion that goes through one end thereof and will receive a piston 116 therein. The body 104 also may include a plurality of orifices 118 through side surfaces thereof such that the orifices 118 create pathways between the inner chamber 114 of the body 104 and the outer surfaces of the body 104. In one embodiment contemplated, there are three orifices 118 arranged therein with two on one side of the body 104 and a third orifice arranged on the opposite side or 180° from one of the other orifices. These orifices 118 generally will receive actuator and locking mechanisms therein. Adjacent to one of the orifices 118 through the surface of the body 104 may be a lip 120 that generally will have a circumferential shape. The lip 120 extends a predetermined distance from the outer surface of the body 104. The lip 120 may act as a protective wall of the actuator button-peg 148 to prevent accidental release. It should be noted that the lip 120 can be of any known cross sectional shape and may be of any shape when viewed from above depending on the type and shape of actuator mechanism used in the subretinal implantation instrument 100. It should be noted that the body 104 may be made of any known material, such as metal, plastic, ceramic, composite or any other known natural or man made material. It should be noted that the body 104 may be formed as one member or as two separate halves that are connected later on during assembly of the instrument 100. It should be noted that the instrument 100 may be a one use instrument 100 or capable of being sterilized and reused if necessary.

A piston 116 is generally arranged partially within the body 104 of the instrument 100. One portion of the piston 116 is arranged within the inner chamber 114 of the body 104. The piston 116 on one end thereof generally may have a predetermined angled surface 122 that interacts with an actuator mechanism 110 of the instrument 100. The predetermined angled end of the piston 116 also may include a locking cavity 124 arranged therein. The locking cavity 124 has any predetermined shape that will generally mimic and interact with the shape of a locking member 126 that is arranged therein. The piston 116 is slidable with relation to the body 104 and may have a portion of the piston 116 arranged within the inner chamber 114 of the body 104 while another portion of the piston 116 extends from one end of the body 104 having the reduced diameter orifice therethrough. Generally, the piston 116 may have a cylindrical type shape except for the angled surface end 122. The outer diameter of the piston 116 generally will be equal to or slightly less than the reduced diameter orifice of the body 104. This will allow the piston 116 to freely slide with relation to the body 104 via a spring 128. Generally, a coil spring 128 is arranged over one portion of the piston 116 and is arranged such that the coil spring 128 engages with a shoulder 130 of the piston 116 on one end thereof and with an inner surface of the inner chamber 114 of the body 104 on the second end thereof. This will allow for the spring 128 to urge the piston 116 in a rearward direction with relation to the body 104 of the instrument 100. It should be noted that any type of spring made of any known material may be used instead of the coil spring 128. The piston 116 also may include a predetermined shaped groove or slot 132 on a bottom surface thereof which will receive a mandrel 102 therein. The piston 116 also may include a vacuum passage 134 arranged in the end of the piston 116 opposite from that of the angled surface end 122. Generally, the vacuum passage 134 has a generally L-shaped cross section when viewed from the side as shown in FIG. 1. This L-shape or hockey stick shaped vacuum passage 134 allows for the insertion of a syringe 112 or tube 136 connected to a syringe 112 in one end of the passage 134 thus allowing for a vacuum or suction to be created such that insertion and orientation of the tissue 108 or implant in the end of the sleeve or nozzle 106 can occur. The piston 116 has a circumferential flange 138 arranged near one end thereof. Generally, the vacuum passage 134 extends from the outer surface of the circumferential flange 138 to the near end of the piston 116. It should be noted that any type of syringe 112 may be used with the vacuum passage 134 and that the syringe 112 may be connected directly to the vacuum passage 134 or use a connection tube 136 as shown in FIG. 1. The piston 116 also may include an orifice of any known size through which the mandrel 102 will be arranged therein. This orifice aligns with the groove 132 described above for the piston 116. Generally, the orifice has a rectangular shape that will mimic that of the mandrel 102. At one end of the piston 116 the mandrel 102 generally may have a seal 140 arranged around the mandrel 102. This seal 140 may be arranged between the surface of the piston 116 on one side thereof and the outer surface of the mandrel 102 on the other side thereof. The seal 140 allows for the vacuum suction of the tissue 108 or implant into the nozzle tip to occur in a more efficient manner.

Figure 2:
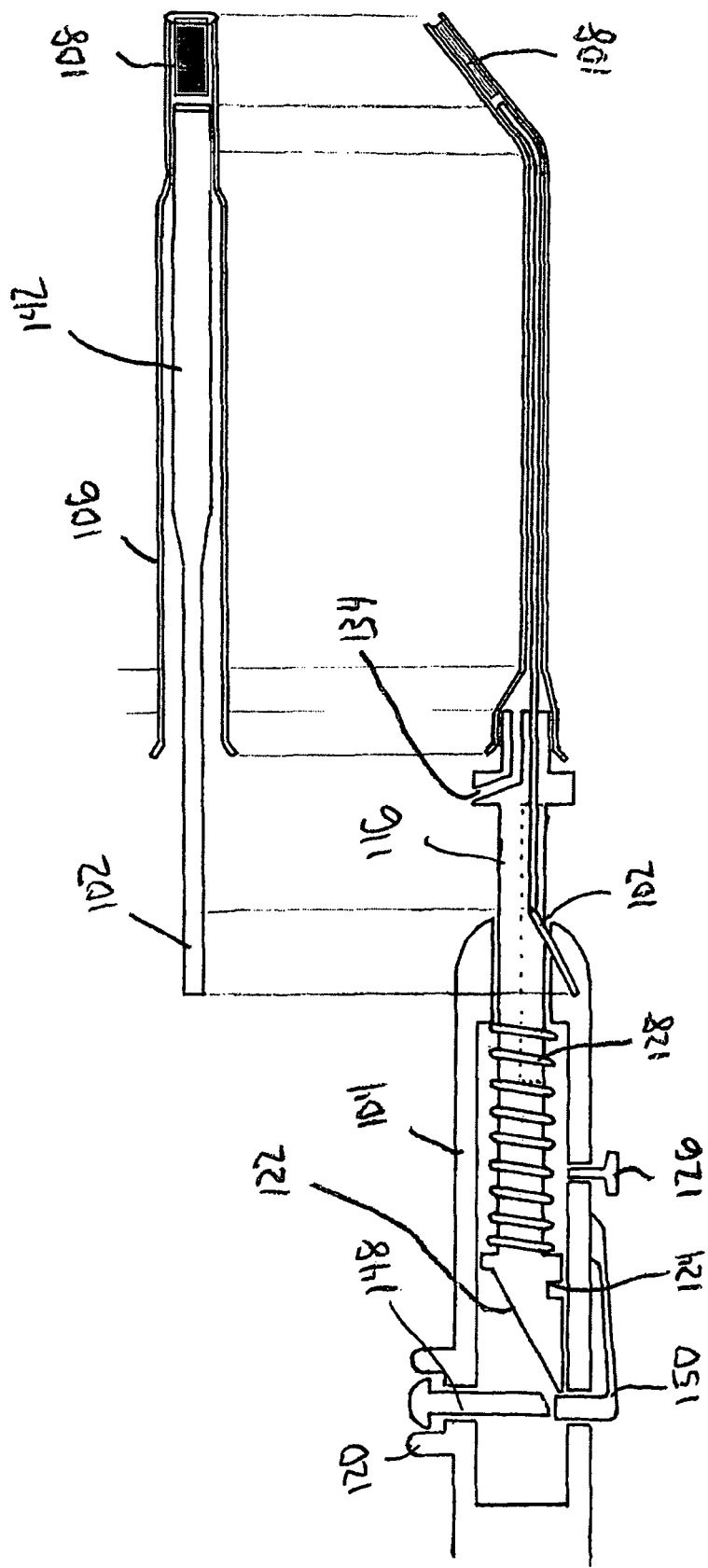
FIG. 2 shows a cross sectional view of the instrument in its loaded and tissue inside the nozzle sleeve position.
Figure 3:
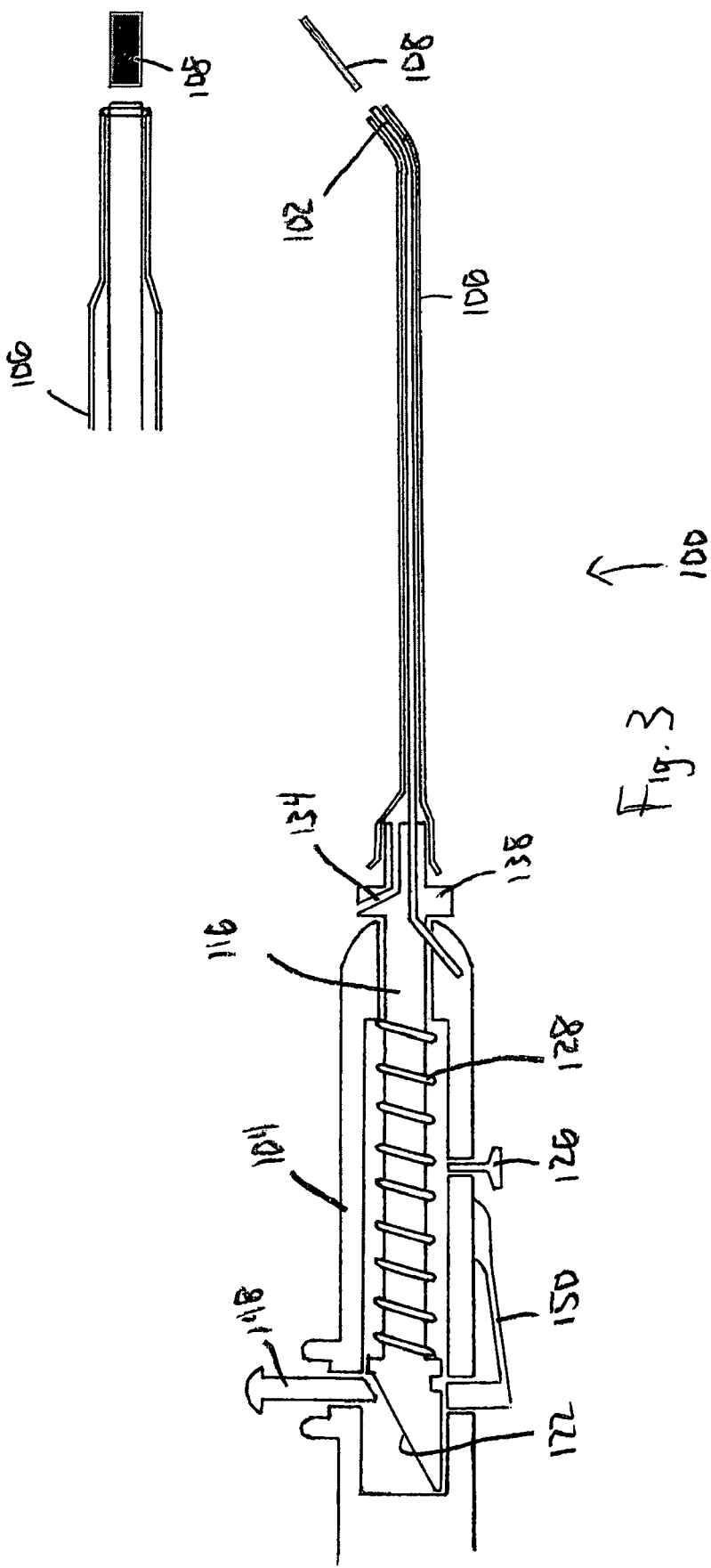
FIG. 3 shows a cross sectional view of the instrument after the instrument is placed in its released position with the nozzle retracted and the tissue placed in the target.

The instrument 100 according to the present invention also comprises an elongated mandrel 102. In one contemplated embodiment the mandrel 102 is an elongated flat and narrow strip of steel that will be fixed to the body 104 but may also be longitudinally adjustable relative thereto. The extension or retraction of the mandrel 102 relative to the body 104 will regulate its longitudinal position relative to the length of the nozzle 106 in the retracted position. It should be noted that the mandrel 102 can be made of any other type of material not just metal, such as but not limited to plastic, ceramic, composite, natural materials or the like. In one embodiment contemplated for the present invention, the mandrel 102 may have an increased width portion 142 near one end thereof as shown in FIG. 2. Using this increased width ensures that there is no space such that suction will occur thus allowing for a more efficient orientation of the tissue 108 within the end of the nozzle 106. It should further be noted that the vacuum passage 134 generally may have a circular cross section, however any other shaped passage way may also be used depending on the design requirements of the instrument 100. Hence, the mandrel 102 will be fixed with relation to the body 104 of the instrument 100. In one embodiment the end of the mandrel 102 will be chemically or mechanically secured to the body 104 near one end thereof in a slot or groove of the body 104. It is contemplated to use a glue, or any other mechanical structure, such as a snap fit mechanism, interference fit mechanism or any other known chemical or mechanical fastening technique. Generally, the mandrel 102 may have a bend with a predetermined angle occur after the mandrel 102 exits from the body 104 surface. The opposite end of the mandrel 102 may or may not have a bend depending on the kind of surgery. For human subretinal eye surgery, the bend of the mandrel should be around 135 for the thin walled flexible nozzle 106 capable to move along relative to the bend of the mandrel 102.

The nozzle or sleeve 106 generally is made of a plastic, such as but not limited to Teflon material, however any other known material such as metal, ceramic, composite, or natural material may also be used for the nozzle 106. The nozzle 106 also may include a reduced neck portion 144 near one end thereof. This neck portion 144 allows for a space to be arranged therein for suction to occur and the front narrow portion allowing for the nozzle 106 to fit tightly around the mandrel 102 with a predetermined amount of space at the tip of the nozzle 106. It should be noted that the tissue 108 should not be sucked into the neck region 144 and that the nozzle 106 tip is flat to prevent the tissue from curling up when in the end of the nozzle 106. Generally, the nozzle 106 has a flat end where the tissue 108 will be stored therein with a predetermined width. Generally, the tip has a rectangular shape when viewed from an end. The nozzle 106 may be of any known shape, but generally has a rectangular shape when viewed in cross section. The opposite end of the nozzle 106 generally has a tight fit over the end tip of the piston 116 that will allow for an effective seal and a vacuum to occur within the nozzle 106 to allow for suction to bring the tissue 108 into proper orientation within the tip of the nozzle 106. It should be noted that an interference fit generally is used to secure the end of the nozzle 106 to the end of the piston 116, however a clamp may be arranged thereover or any other chemical bonding or mechanical fastening technique may be used to secure the nozzle 106 to the end of the piston 116 to ensure a tight seal that is capable of drawing a vacuum therein. It should be noted that the angle of the mandrel 102 can vary depending on what body part the instrument 100 will be used for implanting tissue or the like therein. The nozzle 106 will be capable of movement relative to the mandrel 102 including any bend or predetermined angles 146 arranged within the mandrel 102 along its length thereof. It should be noted that in cross section the mandrel 102 may have a generally L-shape or hockey stick shape.

The instrument 100 also may include an actuator mechanism 110 arranged in the body 104 of the instrument 100. The actuator mechanism 110 may include an actuator button or peg 148 and an actuator spring 150. However, it should be noted that the actuator button 148 and spring 150 in one contemplated embodiment are made of plastic, however any other type of metal, ceramic, composite, or natural material may be used for both the actuator spring 150 and actuator button peg 148. The actuator button or peg 148 may have an angled surface 152 on one end thereof wherein that end thereof is arranged within the inner chamber 114 of the body 104. The actuator spring 150 generally has an L-shape and will have the short portion of the L-shape arranged within an orifice 118 of the body 104 of the instrument 100. The other end of the actuator spring 150 may be secured to an outer surface of the body 104 via any known securing technique, including but not limited to any chemical fastening technique or any mechanical fastening technique. In its neutral position the actuator button 148 will extend a predetermined distance away from the outer surface of the body 104 yet generally within or along the circumferential lip 120 described above to protect from accidental release of the actuator button-peg. The actuator spring 150 also may extend a predetermined distance within the inner surface of the inner chamber 114 of the body 104 in its neutral position. As shown in FIG. 1, a locking member 126 is arranged through another orifice of the body 104 and interacts with the locking cavity 124 of the piston 116. The locking member 126 may be arranged within the orifice such that its end is arranged within the locking cavity 124 and engages therewith. This will secure that the piston 116 places the neck of the nozzle 106 with relation to the tip of the mandrel so that the surgeon can suction the tissue 108, to be implanted, into the end of the nozzle 106. The locking member 126 may be of any known shape however, the shape shown is generally in the shape of a pin, nail or screw, etc. It should be known that any other known shape may be used for the locking member 126 as long as it interacts with the locking cavity 124 of the piston 116. The locking member 126 also may be arranged within the orifice of the body 104 such that it releases to a predetermined position such that the end of the locking member 126 is equal to or recessed from the inner surface of the inner bore of the body 104. This will allow for the locking member 126 to always be secured to the body 104 but to retract such that the piston 116 can slide relative to the body 104 within the inner chamber 114 of the instrument 100. However, it is also contemplated that the locking member 126 may be completely removed from the body 104 after it is removed from the locking cavity 124 of the piston 116.

In operation, the surgeon will engage the locking member 126 with the locking cavity 124 of the piston 116 prior to beginning the suction or sucking of the tissue 108 into the nozzle 106. It should be noted that the tissue or implant 108 may have any known shape along with the nozzle 106 also having any known shape. After the piston 116 is locked by the locking member 126 with relation to the body 104 of the instrument 100 the surgeon will attach the end of a syringe 112, either via a tube connection 136 or via the syringe 112 directly to one end of the suction vacuum passage 134 of the piston 116. The surgeon will then align the end of the nozzle 106 with the tissue or implant 108 to be placed within the eye or other body part of the person being operated on. The surgeon will then pull back on the syringe 112 creating a vacuum which creates suction within the nozzle 106, thus urging the tissue or implant into the tip of the nozzle 106 via the suction being afforded by the syringe 112. If the implant has a polarity like a sheet of retina, the surgeon will orient the implant in the right position before suction so they will be 100% sure they deliver the implant in the right orientation. The tissue 108 also should not be sucked into the wider neck region of the nozzle 106. It should also be noted that the nozzle sleeve tip is narrow and flat to prevent the tissue from curling up after insertion into the end of the nozzle 106. However, any other known or shaped nozzle 106 and nozzle tip may also be used with the present invention.

FIG. 2 shows the instrument 100 according to the present invention, loaded, after the tissue 108 has been placed into the nozzle 106. After the tissue 108 has been drawn up into the nozzle 106 to the appropriate position, the surgeon will pull the locking member 126 out away from the locking cavity 124 of the piston 116 which will allow the piston 116 to automatically move via the spring force of the coil spring 128 but in a controlled way by the surgeon holding the circumferential flange 138 of the piston 116, to the locked/loaded position wherein the piston 116 will be engaged with or held by the plastic spring 150 on one end. Therefore, after the instrument 100 is loaded the end of the piston 116 will be engaged with the actuator spring 150 within the inner bore 114 of the body 104.

Next, the surgeon will "release" the instrument 100 thus allowing the nozzle 106 to be retracted and the tissue 108 placed in its proper target position. The surgeon will press the actuator button or peg 148 in a downward motion such that the actuator button 148 will engage the actuator spring 150 and move the actuator spring 150 in a direction away from the inner bore 114 of the body 104 thus disengaging the actuator spring 150 from the piston 116 and hence allowing the piston 116 to move further in a backward direction with respect to the body 104. This backward motion of the piston 116 occurs via the coil spring 128 urging the piston 116 in a rearward direction or backward direction with relation to the body 104. The actuator button or peg 148 after moving the actuator spring 150 out of engagement with the end of the piston 116 will engage, via its angled surface 152, with the angled surface 122 of the piston 116 and allow for the surgeon to control manually the retraction of the tissue 108 from the end of the nozzle 106. This rearward movement of the piston 116 will expose the tissue 108 that was previously covered by the nozzle 106 into the appropriate position in the back of the eye or other body part.

Figure 4:
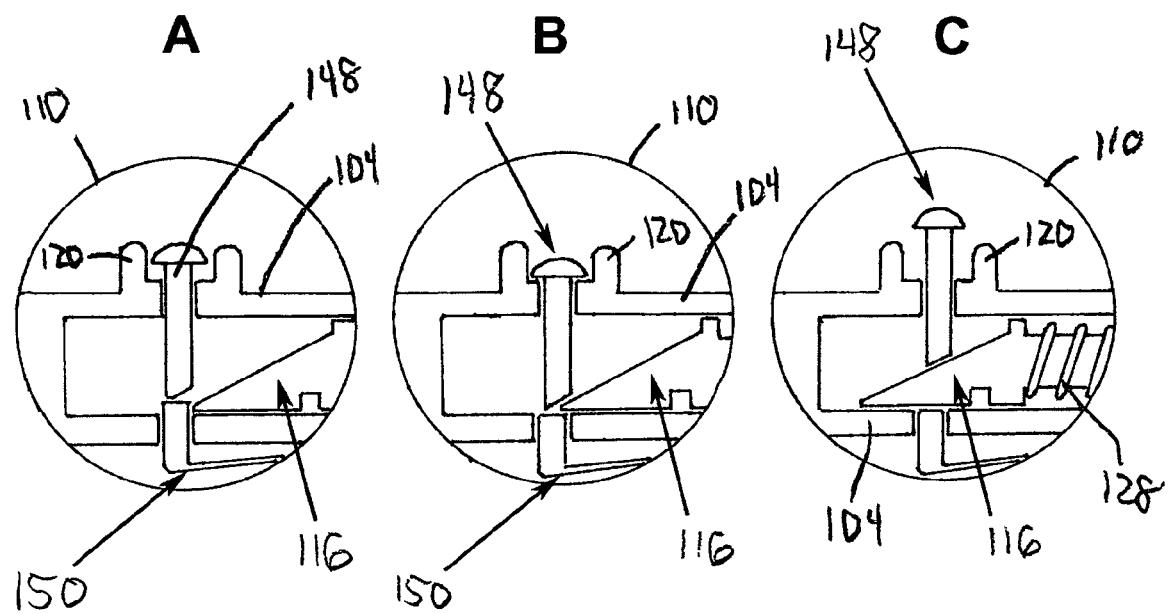
FIGS. 4a through 4c show the actuator and release mechanism according to the present invention in different positions.
Figure 5:
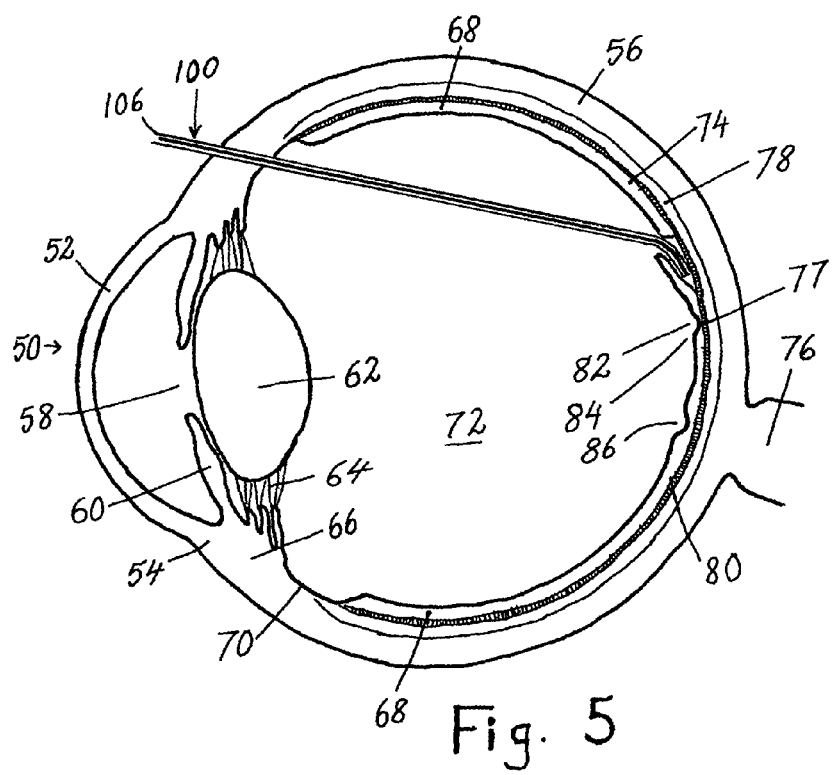
FIG. 5 shows a cross sectional view of the human eye showing an implantation instrument inserted through the pars plana into the subretinal space.

As shown in FIG. 4 the loaded position of the actuator mechanism 110 shows that the end of the moveable piston 116 may be locked in engagement with the actuator spring 150 as shown in FIG. 4a. FIG. 4b shows the actuator button or peg 148 being fully depressed by the surgeon thus disengaging the actuator spring 150 from the piston 116 and releasing the piston 116 to move in a rearward direction with respect to the body 104 wherein that backward movement is controlled by the surgeon via the button-peg angled surface 152 interacting with the angled surface 122 of the piston 116. The releasing of the pressure by the surgeon via the actuator button 148 by his or her finger tip will allow for the surgeon to hold his hand completely still and only have to move a finger thus allowing the piston 116 to be pushed back by the coil spring 128. The piston 116 with the attached nozzle 106 being retracted in a rearward direction will allow for the tissue 108 inside the tip to be placed in the target area via the mandrel 102. It should be noted that this will allow the tissue 108 to be placed in a proper position and not pushed or injected into the target area. It should be noted that the hand piece and mandrel 102 are not required to move incident to deposition of the retinal tissue allowing the surgeon to precisely position the tissue within the back of the eye or other body part. Once the surgeon places the nozzle 106 in its proper position no further movement of the hand of the surgeon or the instrument 100 is necessary other than the finger tip to control the release of the tissue 108 in its position via the nozzle 106 sliding backwards. It should be noted that any type of materials routinely utilized for surgery can be used to make any of the components of the instrument. It should also be noted that the methodology described for implanting the tissue or implant can be used in any body member not just the eye as described herein.

From the foregoing it should be apparent that the instrument of the present invention accepts sheets of retinal tissue in an efficient manner and thereafter precisely implants the tissue 108 into the eye 50. The surgeon has only to keep his hand still and exert pressure on the actuator button or peg 148 of the instrument 100 to release the piston 116 and allow for the piston 116 to be retracted in a smooth and efficient manner to effect retraction of the nozzle 116 and placement of the implant on the target area.

While the preferred embodiment of the invention has been disclosed, it should be appreciated that the invention is susceptible of modification without departing from the scope of the following claims. Furthermore, many modifications and variations of the present invention are possible in light of the above teachings, therefore within the scope of the appended claims, the present invention may be practiced otherwise than as specifically described.

What is claimed is:

1. An instrument for implanting tissue in an eye or other body member comprising:
   an elongated mandrel;
   a tubular nozzle arranged over said mandrel;
   a piston secured to and engaging an end of said nozzle;
   a vacuum passage arranged in said piston;
   a body having a portion of said piston arranged therein, one end of the mandrel is secured to and engages said body, said piston slides with relation to said body; and
   an actuator integrated with said body, said actuator interacts with said piston to control movement of said nozzle relative to said mandrel.

2. The instrument of claim 1 further comprising a syringe connected to said vacuum passage.

3. The instrument of claim 2 further comprising a tube arranged between said syringe and said vacuum passage.

4. The instrument of claim 2 wherein said syringe uses suction to pick up the tissue inside an end of said nozzle.

5. The instrument of claim 1 further comprising a seal arranged between said mandrel and said piston.

6. The instrument of claim 1 further comprising a spring arranged between said piston and an internal surface of said body.

7. The instrument of claim 6 wherein said spring is a coil spring.

8. The instrument of claim 1 wherein said actuator comprising a button or peg and a spring, said button or peg passes through an orifice of said body, one end of said spring passes through an orifice of said body.

9. The instrument of claim 8, wherein said spring is connected to an inner surface of said body at another end thereof.

10. The instrument of claim 8 wherein said button moves said spring when said button is pressed.

11. The instrument of claim 1 further comprising a lock member arranged through an orifice of said body, said lock member interacts with a cavity of said piston.

12. The instrument of claim 8 wherein said button having an angled surface on an end thereof, said piston having an angled surface on an end thereof, said angled surfaces engage with one another when the instrument is released in order to properly and smoothly place the tissue.

* * * * *